(12) United States Patent
Rigney

(10) Patent No.: US 9,285,545 B2
(45) Date of Patent: Mar. 15, 2016

(54) COMPRESSIVE SENSING IMAGING SYSTEM

(71) Applicant: Southwest Research Institute, San Antonio, TX (US)

(72) Inventor: Michael P. Rigney, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 224 days.

(21) Appl. No.: 14/186,921

(22) Filed: Feb. 21, 2014

(65) Prior Publication Data

US 2015/0243698 A1  Aug. 27, 2015

(51) Int. Cl.
*H01L 27/146* (2006.01)
*G02B 6/32* (2006.01)
*G02B 6/26* (2006.01)

(52) U.S. Cl.
CPC . *G02B 6/32* (2013.01); *G02B 6/262* (2013.01)

(58) Field of Classification Search
CPC .................. H01L 27/14634; H01L 27/14625; G02B 6/262; G02B 6/32
USPC ...................................................... 250/208.1
See application file for complete search history.

(56) References Cited

U.S. PATENT DOCUMENTS 8,860,835 B2 * 10/2014 Kelly et al. ........ G02B 26/0833 348/222.1
2011/0025870 A1  2/2011  Baraniuk et al.

OTHER PUBLICATIONS

R.G. Baraniuk, "Compressive Sensing"; IEEE Signal Processing Magazine, lecture Notes, Jul. 2007, pp. 118-120 and 124.
E.J. Candes, et al, "An Introduction to Compressive Sampling, a Sensing/sampling Paradigm That Goes Against the Common Knowledge in Data Acquistion", IEEE Signal Processing Magazine, Compressive Sampling, Mar. 2008, pp. 21-30.
M.F. Duarte, et al; "Single-Pixel Imaging via Compressive Sampling, Building Simpler, Smaller, and Less-expensive Digital Cameras"; IEEE Signal Processing Magazine, Compressive Sampling, Mar. 2008, pp. 83-91.
R. Fergus, et al, "Random Lens Imaging"; Computer Science and Artificial Intelligence Laboratory Technical Report, MIT-CSAIL-TR-2006-058, Sep. 2, 2006 (11 pgs).
Myriad Fiber Imaging Tech., Inc.; "Myriad Fiber Imaging"; http://www.myriadfiber.com/fujikura-image-fiber-specs.html.
R.N. Mahalati, et al; "Resolution Limits for Imaging Through Multimode Fiber"; Optics Express, Jan. 14, 2013, vol. 21, No. 1, pp. 1656-1668.

(Continued)

*Primary Examiner* — Seung C Sohn
(74) *Attorney, Agent, or Firm* — Grossman, Tucker et al

(57) ABSTRACT

The present disclosure relates to a compressive sensing imaging system which may include a compressive sensing optic (CSO) that includes a plurality of compressive sensing elements (CSEs), a fiber optic bundle (FOB) that includes a plurality of fiber optic elements (FOEs) and a sensor that includes a plurality of optical sensing elements (OSEs). Each CSE is configured to capture a respective random CSE optical sample related to a respective portion of a scene and to provide the respective CSE optical sample to the FOB. Each FOE is configured to integrate one or more accepted scene optical samples to produce an associated compressed optical sample and each scene optical sample corresponds to at least a portion of a respective CSE optical sample. Each FOE is further configured to provide the associated compressed optical sample to the sensor. Each OSE is configured to integrate one or more received sensor optical samples.

22 Claims, 9 Drawing Sheets

(56) References Cited

OTHER PUBLICATIONS

J. Romberg, "Imaging Via Compressive Sampling, Introduction to Compressive Sampling and Recovery Via Convex Programming"; IEEE Signal Processing Magazine, Compressive Sampling, Mar. 2008, pp. 14-20.

R.M. Willett, et al; "Compressed Sensing for Practical Optical Imaging Systems: A Tutorial"; Optical Engineering 50(7), pp. 072601-1 to 072601-13, Jul. 2011; Downloaded From: http://opticalengineering.spiedigitallibrary.org/ on Dec. 11, 2013 Terms of Use: http://spiedl.org/terms.

* cited by examiner

COMPRESSIVE SENSING IMAGING SYSTEM

FIELD OF THE INVENTION

This disclosure relates to an apparatus, system and method configured for capturing optical samples related to an object and/or scene.

BACKGROUND

Image resolution from imaging systems utilized in relatively tightly constrained spaces may be limited due to constraints imposed in accessing those spaces. Examples of such imaging systems include borescopes, endoscopes and videoscopes.

SUMMARY

The present disclosure relates in one embodiment to an apparatus. The apparatus includes a compressive sensing optic (CSO) that includes a plurality of compressive sensing elements (CSEs). Each CSE is configured to capture a respective random CSE optical sample and each CSE optical sample is related to a respective portion of a scene. The apparatus further includes a fiber optic bundle (FOB) coupled to the CSO at a first end of the FOB. The FOB includes a number of fiber optic elements (FOEs). Each FOE is configured to integrate one or more accepted scene optical samples to produce an associated compressed optical sample and each scene optical sample corresponds to at least a portion of a respective CSE optical sample. Each CSE is configured to provide the respective CSE optical sample to the FOB and each FOE is configured to carry the associated compressed optical sample from the first end to a second end of the FOB configured to be coupled to a sensor.

The present disclosure relates in one embodiment to a system. The system includes a compressive sensing optic (CSO) that includes a plurality of compressive sensing elements (CSEs). Each CSE is configured to capture a respective random CSE optical sample and each CSE optical sample is related to a respective portion of a scene. The system further includes a fiber optic bundle (FOB) coupled to the CSO at a first end of the FOB. The FOB includes a number of fiber optic elements (FOEs). Each FOE is configured to integrate one or more accepted scene optical samples to produce an associated compressed optical sample. Each scene optical sample corresponds to at least a portion of a respective CSE optical sample. The system further includes a sensor coupled to a second end of the FOB. The sensor includes a plurality of optical sensing elements (OSEs) and each OSE configured to integrate one or more received sensor optical samples. Each CSE is configured to provide the respective CSE optical sample to the FOB, each FOE is configured to provide the associated compressed optical sample to the sensor and each sensor optical sample corresponds to at least a portion of a respective compressed optical sample.

The present disclosure relates in another embodiment to a method. The method includes capturing, by each compressive sensing element (CSE) of a plurality of CSEs in a compressive sensing optic (CSO), a respective random CSE optical sample related to a respective portion of a scene. The method further includes providing, by each CSE, the respective CSE optical sample to a fiber optic bundle (FOB) comprising a plurality of fiber optic elements (FOEs). The method further includes integrating, by each FOE, one or more accepted scene optical samples to produce an associated compressed optical sample, wherein each scene optical sample corresponds to at least a portion of a respective CSE optical sample.

BRIEF DESCRIPTION OF THE DRAWINGS

The detailed description below may be better understood with reference to the accompanying figures which are provided for illustrative purposes and are not to be considered as limiting any aspect of the invention.

DETAILED DESCRIPTION

In general, the present disclosure describes an apparatus, system and method configured to compressively sample a scene to facilitate generating an image of the scene. The scene may include an object. Compressive sensing, also known as compressed sampling, is configured to allow a relatively higher resolution image to be inferred from a relatively smaller number of measurements.

A basic idea of compressed sensing theory is that when an image is "sparse" in some basis (i.e., most basis coefficients are relatively small and/or zero), a relatively small number of selected observations may be sufficient to reconstruct the most significant nonzero components. The most significant nonzero components may then be utilized to reconstruct the image. For example, a wavelet transform of an image of a scene may be relatively sparse. In other words, the wavelet transform may include a relatively small number of elements with values greater than some threshold. The image may be reconstructed from wavelets above the threshold. In other words, an image of a scene X that includes N image samples (x(n), n=1, ..., N) may be represented by M (M<N) measurements (y(m), m=1, ..., M). For example, the measurements may correspond to $y(m)=(x, \Phi_m)$, where the brackets correspond to an inner product. A matrix $\Phi$ may be formed of transpose test functions $\Phi_m^T$, then $y=\Phi x$. According to compressive sensing theory, by appropriate selection of $\Phi$, uncompressed optical image data that corresponds to the scene X may be recovered from the measurements y(m). For example, each measurement y(m) may correspond to a combination of a respective subset of random image samples x(i), i=1, ..., R. An image of the scene (i.e., uncompressed optical image data) may then be recovered using one or more reconstruction techniques, e.g., convex optimization, basis pursuit, greedy algorithms (e.g., matching pursuit, orthogonal matching pursuit), etc.

A compressive sensing imaging system consistent with the present disclosure is configured to capture a plurality of optical samples. Each optical sample corresponds to optical energy associated with a portion of a scene to be imaged. The system is further configured to integrate a plurality of subsets of random optical samples (and/or portions thereof) to produce a plurality of compressed optical samples. Each compressed optical sample may then correspond to a combination of random optical samples, i.e., may correspond to a measurement. In some embodiments, the compressive sensing imaging system may be configured to further randomize and integrate pluralities of portions of the compressed optical samples. In these embodiments, the integrated portions correspond to measurements. The compressive sensing imaging system is configured to convert the measurements to electrical samples and to digitize and process the electrical samples to recover an image of the scene.

Figure 1:
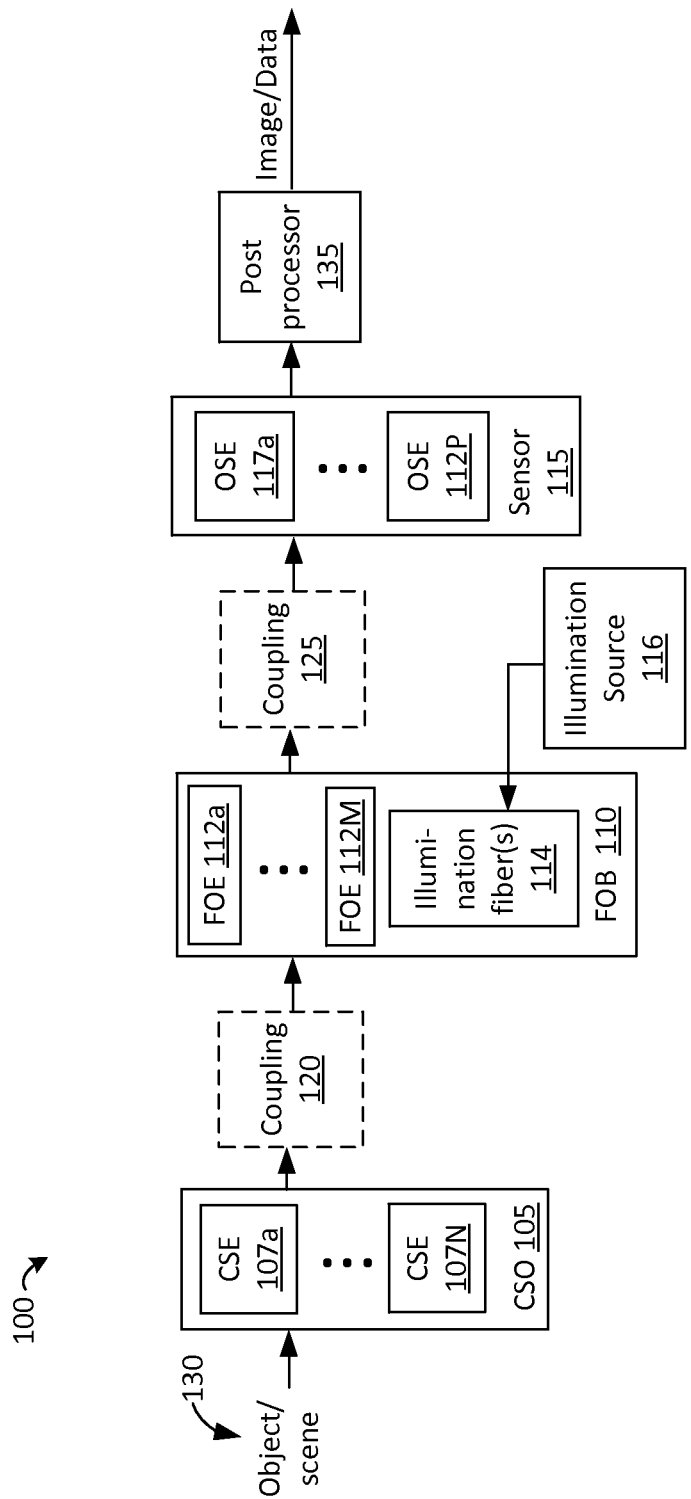
FIG. 1 depicts an exemplary system block diagram of a compressive sensing imaging system consistent with the present disclosure.

Attention is directed to FIG. 1 which depicts a system block diagram of a compressive sensing imaging system 100, consistent with the present disclosure. The system 100 is configured to capture a plurality of optical samples that correspond to portions of scene 130, combine subsets of random optical samples and to recover an image of the scene based, at least in part, on the combined samples. The system 100 includes a compressive sensing optic (CSO) 105, a fiber optic bundle (FOB) 110 and sensor 115. The CSO 105 includes a plurality of compressive sensing elements (CSEs) 107a, ..., 107N. The FOB 110 includes a plurality of fiber optic elements (FOEs) 112a, ..., 112M. The sensor 115 may include a plurality of optical sensing elements (OSEs) 117a, ..., 117P. The system 100 may include a first coupling 120 configured to couple the CSO 105 to the FOB 110 and/or a second coupling 125 configured to couple the FOB 110 to the sensor 115. The system 100 may include a post processor 135 configured to recover an image of the scene 130 from a plurality of measurements, as described herein.

The system 100 may include one or more illumination fiber(s) 114 and an illumination source 116. Illumination fiber(s) 114 are configured to carry illumination from the illumination source 116 to illuminate the scene 130. Illumination field may thus correspond to the scene or an object and/or portion thereof illuminated by illumination fiber (s) 114.

Illumination source 116 is configured to provide optical energy of a selected wavelength and/or range of wavelengths to illumination fiber(s) 114. The selected wavelength and/or range of wavelengths may be related to a type of sensor 115 (e.g., image sensor, photomultiplier) and/or a compressive sensing application. For example, illumination source 116 may be configured to provide optical energy corresponding to visible light (e.g., wavelength range of about 400 nm (nanometers) to about 700 nm). In another example, illumination source 116 may be configured to provide near-infrared (NIR) optical energy (e.g., wavelength range of about 700 nm to about 1 µm (micrometer)). In another example, illumination source 116 may be configured to provide infrared optical energy (e.g., wavelength range of about 1 µm to about 12 µm). In another example, illumination source 116 may be configured to provide ultraviolet a (UVa) optical energy (e.g., wavelength range of about 100 nm to about 400 nm). UVa optical energy may result in visible band fluorescence that may then be captured.

The illumination fiber(s) 114 are configured to carry optical energy, e.g., light, from the illumination source 116 to a first end of FOB 110 (adjacent the scene) and to emit the optical energy onto the scene 130. Thus, illumination fiber(s) 114 may be configured to illuminate at least a portion of scene 130. For example, illumination fibers 114 may be included in FOB 110. In another example, illumination fibers 114 may be coupled to FOB 110. Illumination fiber(s) 114 may be terminated at the first end of FOB 110 with an optical cover and/or a diffuser configured to distribute the illumination energy from the illumination fiber(s) 114 to the scene 130.

Illumination fiber(s) 114 may be formed of a material configured to carry optical energy of a desired spectrum (i.e., range of wavelengths). For example, silica may be used to form glass optical fibers. Glass optical fibers may be configured to carry optical energy in the visible and/or infrared ranges. In another example, illumination fibers may formed of plastic. In another example fluoride glass composed of fluorides of various metals may be used. Heavy metal fluoride glass such as a ZBLAN (zirconium, barium, lanthanum, aluminum, and sodium fluorides) glass group may be utilized for the mid-IR (e.g., 2000 nm to 5000 nm) range. Illumination fiber(s) 114 (and associated materials) may thus be selected based on desired spectrum (i.e., range of wavelengths).

The CSO 105 is a static optical device that is configured to incoherently sample the illumination field associated with the scene 130 that is within its field of view onto an input face (i.e., first end) of the FOB 110. Incoherently sampling means that a spatial relationship between positions in the illumination field is generally not preserved on the input face of the FOB 110. For example, a single point and/or region of the scene 130 may map to a plurality of FOEs (112a, ... 112M) on the input face of the FOB 110 rather than a single FOE. In another example, a plurality of randomly positioned scene portions may map to one FOE, e.g., FOE 112a.

A static optical device is configured to capture optical samples corresponding to the scene or portion of the scene that is within its field of view without being actively repositioned in order to capture the optical samples. The CSO 105 may thus not require electrical power at the first end of the FOB 110. Of course, the CSO 105 may be repositioned to capture a different scene, the scene 130 from a different perspective (e.g., location) and/or a different portion of the scene 130.

Each CSE 107a, ..., 107N is configured to capture a CSE optical sample corresponding to a respective scene portion. Each CSE optical sample includes optical energy (e.g., light intensity) associated with the respective scene portion. A size of a scene portion captured may be related to characteristics of the associated CSE 107a, ..., 107N. Thus, respective sizes of a plurality of scene portions captured by CSEs 107a, ..., 107N may vary.

CSEs 107a, ..., 107N may include, but are not limited to, random lenses, random mirrors, a microlens array, a micromirror array, a diffractive optic and/or a diffraction grating. Lenses may be concave, convex and/or may include one planar surface. Lens focal lengths may vary and may range from relatively short to relatively long. Lens focal length is related to angle of view and, therefore, a size of a scene portion. Minor elements may be planar, concave and/or convex. CSE 107a, ..., 107N position and/or orientation may vary within the CSO 105. The plurality of CSEs 107a, ..., 107N are configured to capture the plurality of random CSE optical samples. Random, as used herein with respect to CSEs, means orientation, position and/or characteristics of the CSEs vary, i.e., are non-uniform. Random, as used herein with respect to CSE optical samples, means location, size and/or orientation of a scene portion represented by a random CSE optical sample vary, i.e., scene optical samples are non-uniform. In a random lens, a collimated beam may not be focused to a single point, rather, one or more rays in the collimated beam may be focused to each of a plurality of points.

Conventional diffractive optics (DOs) may typically be configured to receive optical energy from, for example, a point source, to diffract the incident optical energy and to produce a pattern, e.g., an array of dots, array of lines and/or a coded array of dots. In an embodiment consistent with the present disclosure, such a DO may be configured to provide a uniform sampling of the scene that corresponds to the pattern the DO is configured to generate from a point source. The random positions of FOEs relative to the DO, and the plurality of FOEs may be configured to yield a compressed random sampling of the scene. The DO may include one or more diffractive optical elements (DOEs) that may be tiled (i.e., stacked next to one another). A pattern DO may define a plurality of DOEs configured to produce multiple overlapping diffraction patterns thus providing a compressed random sampling of the scene.

A diffraction grating generally provides wavelength-dependent dispersion of light. In an embodiment consistent with the present disclosure, one or more diffraction gratings may be included in the CSO 105 to spectrally disperse CSE optical samples. Different wavelengths (i.e., colors) present in CSE optical samples may thus be integrated into different compressed optical samples. A tiled DO may be configured to include a combination of DOEs (spatial sampling) and diffraction grating elements (spectral sampling).

A microlens array may include a plurality of lens elements and a substrate. The lens elements may be formed on or in the substrate, and/or formed separately and attached to the substrate. Because of the relatively small size of microlenses, the substrate may be thicker than the lens element. Each of the plurality of microlens elements in the microlens array may be configured as one or more of: a) a single element with one planar surface and one spherical convex surface to refract the optical energy, b) a single element with two aspherical surfaces, c) a plurality of layers of optical material configured to refract optical energy, d) a gradient-index lens, e) a micro-Fresnel lens and/or f) a binary-optic microlens. A gradient-index lens (GRIN) is a single element with two parallel planar surfaces where refraction is achieved via a variation of refractive index across the lens. A micro-Fresnel lens is configured to refract optical energy in a set of concentric curved surfaces. Such lenses can be made very thin and lightweight. Binary-optic microlenses are configured to diffract optical energy. Binary-optic microlenses may include grooves with stepped edges or multilevels that approximate an ideal shape.

Each lens element is configured to capture a portion of the scene 130. The portion of a scene captured may depend, at least in part, on characteristics of the lens element, position of the lens element and/or the orientation of the lens element relative to the FOB 110 and/or FOEs 112a, . . . , 112M. Characteristics of lens elements may include lens element thickness, lens element nominal geometry (e.g., convex, concave, combination of planar and convex or concave, etc.) and/or distortion related to aberration. Aberrations may include, but are not limited to spherical aberrations, coma, chromatic aberration, field curvature, barrel distortion, pin cushion distortion and astigmatism. Spherical aberration is related to lens shape and results in rays parallel to the lens axis being focused a different distance from the lens centerline depending on respective ray distance from the lens axis. Coma may occur when an object off the lens axis is imaged so that rays pass through the lens at an angle relative to the lens axis. Rays that pass through outer margins of the lens element may be focused at points closer to or further from the lens axis. Chromatic aberration is related to dispersion in the lens element material, i.e., variation in refractive index of lens material with wavelength. An astigmatic lens element has different focal lengths in two perpendicular directions, e.g., horizontal and vertical.

A diameter of each lens element may be related to a diameter of each FOE. In an embodiment, the diameter of a lens element may range from equivalent to the diameter of an FOE to about three times the diameter of the FOE. In another embodiment, the diameter of a lens element may range from one quarter to the diameter of an FOE to equivalent to the diameter of the FOE. For example, for an FOE of diameter 10 µm, each lens element may have a diameter of 2.5 µm to 10.0 µm. The relationship between lens element diameter and FOE diameter is configured to facilitate provision of each of a portion of a plurality of CSE optical samples to each FOE. The lens elements may be oriented in the microlens array so that each lens element axis is randomly aligned with respect to the axis of the FOEs, i.e., randomly aligned with respect to a respective fiber axis of each FOE 112a, . . . , 112M. Thus, a random mapping may be provided between the CSE optical samples and the FOEs 112a, . . . , 112M. Respective focal lengths of each lens element may vary in the microlens array thus providing variation in the size of the scene portion captured by each lens element.

Random minors are configured to facilitate capturing compressed optical image data when an FOB (i.e., an axis of the FOB) is not aligned with the scene to be imaged. A random minor may include a plurality of reflective (i.e., minor) surfaces and/or elements, i.e., CSEs. The minor surfaces and/or elements may be randomly positioned and/or oriented similar to a random lens array. Each reflective surface and/or element may have an associated size. For example, a rectangular element (and/or surface) may have an associated length and width. For example, each of the length and the width may be in the range of one quarter of the FOE diameter to four FOE diameters. Each reflective surface and/or element may be oriented (e.g., positioned) randomly and/or pseudo-randomly with respect to a respective position of each other reflective surface and/or element. Reflective surfaces may be planar, concave, convex and/or a combination thereof. Concave surfaces may be configured to converge incident rays and convex surfaces may be configured to disperse incident rays. A range of reflective surface orientations may be constrained according to, e.g., a desired field of view. For example, a random mirror may be constructed (i.e., formed) by aggregating the plurality of individual reflective elements onto a substrate. In another example, the random mirror may be formed by surface modification of a substrate to produce a plurality of reflective surfaces on the substrate surface.

The CSO 105 may include one or more types of CSEs. For example, CSO 105 may include a random minor configured to capture optical energy corresponding to a plurality of random scene portions and a microlens array to optically couple the random mirror to the FOB 110, thereby providing a plurality of CSE optical samples to the FOB 110. In this example, random sampling of the scene may be enhanced by the combination of the random minors and the random lenses in CSO 105.

The CSO 105 and/or CSEs 107a, . . . , 107N may be formed of a number of materials. For example, materials may include a glass. The glass may be formed of, e.g., silica (silicon dioxide). The glass may include materials other than $SiO_2$. In another example, materials may include a plastic, e.g., acrylic. Mirror surfaces (random mirror, random micromirror array) may be formed from a bulk reflective material or may be formed by application of a reflective coating to a substrate.

The CSO 105 is configured to provide a respective subset of random CSE optical samples to each FOE 112a, ..., 112M in FOB 110. In an embodiment, a respective plurality of CSEs 107a, ..., 107N may be configured to provide captured CSE optical samples to one FOE. For example, the CSO 105 may be positioned relative to FOB 110 so that a distance between the CSO 105 and the first end of the FOB 110 is zero. In another example, characteristics of the CSEs relative to the FOEs may be such that a size of an image plane associated with each CSE is less than an area of a face of each FOE, as described herein. In another example, the CSO 105 may be formed on the first end of the FOB 110. In another embodiment, one or more CSE(s) 107a, ..., 107N may be configured to provide at least a portion of a captured CSE optical sample to a plurality of FOEs. For example, the CSO 105 may be positioned a nonzero distance from a first end of FOB 110. In this example, compressive sensing imaging system 100 may include coupling 120. Coupling 120 may be configured to fix CSO 105 to FOB 110 and to facilitate coupling captured optical energy from CSO 105 to FOB 110. In another example, characteristics of the CSEs relative to the FOEs may be such that a size of an image plane associated with each CSE is greater than an area of a face of each FOE, as described herein.

Each FOE 112a, ..., 112M is configured to accept optical energy that is within an associated acceptance angle and acceptance cone, as described herein. The optical energy may correspond to a portion or all of a CSE optical sample. As used herein, a scene optical sample corresponds to the at least a portion of a CSE optical sample that is within the acceptance cone and acceptance angle of an FOE. Each FOE may thus accept a respective subset of scene optical samples. Each FOE 112a, ..., 112M is configured to integrate the respective subset of the scene optical samples to produce a respective compressed optical sample. A number of compressed optical samples is related to a number M of FOEs 112a, ..., 112M in FOB 110 and is less than a number of CSE optical samples. The number of compressed optical samples may be less than or equal to the number of FOEs 112a, ..., 112M in FOB 110. For example, the number of compressed optical samples may be less than the number of FOEs if fewer than all of the FOEs accept CSE optical samples.

As described herein, FOB 110 includes a plurality of FOEs 112a, ..., 112M. For example, FOB 110 may include at least about 1500 FOEs, up to about 100,000 FOEs. Each FOE may have a diameter of greater than 1 µm, e.g., a diameter of about 5 µm to about 10 µm. A number of FOEs in an FOB may be related to a diameter of the FOB. For example, an about 700 µm diameter FOB may include about 6000 FOEs. In another example, an about 4200 µm diameter FOB may include about 100,000 FOEs. Each FOE may have a substantially circular cross-section. The FOB 110 may have an associated cross-section that may also be substantially circular.

An FOE and/or FOB may be formed of a glass or plastic material. For example, a glass FOE may be formed of silica (silicon dioxide). In another example, a glass FOE may include a fluoride glass such as fluorozirconate or fluoroaluminate. In yet another example, a glass FOE may include a chalcogenide glass. Plastic FOEs may be formed of polymer materials such as PMMA (poly methylmethacrylate) (acrylic), polystyrene or a polycarbonate. FOEs formed of glass may provide lower propagation losses compared to FOEs formed of plastic. FOEs formed of a plastic material may be mechanically more robust and flexible than FOE formed of a glass material and may be lower cost.

CSO 105 may be positioned a distance from the FOB 110. In an embodiment, a value of distance may be related to FOE diameter. In this embodiment, the distance may correspond to a multiple of FOE diameter. For example, the multiple may be in the range of three to five. In another example, the multiple may be in the range of zero to three. When distance is at or near zero, CSO 105 may be attached to FOB 110 and/or CSEs 107a, ..., 107N may be formed on the first ends of each FOE 112a, ..., 112M.

The CSO 105 may be coupled (e.g., mechanically) to the FOB 110 by, e.g., the first coupling 120. For example, the coupling 120 may be formed of material with a similar refractive index to CSO 105 and/or FOEs 112a, ..., 112M. The coupling 120 may be configured to facilitate optical coupling between CSO 105 and FOEs 112a, ..., 112M. For example, the first coupling may be an adhesive, e.g., when FOE 110 is glass or plastic. In another example, the CSO 105 may be fused to the FOB 110 using temperature. In yet another example, FOB 110 may be coupled to the CSO 105 with an air gap between the CSO and the first end of the FOB 110. In an embodiment, the first end of the FOB 110 may be processed, e.g., machined, to form the CSO 105. In this embodiment, individual FOEs 112a, ..., 112M of FOB 110 may be processed to achieve a random lens functionality (e.g., random optical axis orientations and/or random focal lengths). In another embodiment, the first end of FOB 110 may be processed, e.g., machined, to form a surface configured to facilitate coupling to the CSO 105. In yet another embodiment, CSO 105 may correspond to a diffractive optic, e.g., a patterned diffraction grating that may be fabricated on the first end of FOB 110.

The CSO 105 is configured to capture the CSE optical samples generally in parallel for the scene and to provide the CSE optical samples to the plurality of FOEs 112a, ..., 112M. The FOB 110 is configured to provide the plurality of compressed optical samples to the sensor 115, also in parallel, thus facilitating a relatively faster frame rate compared to serial transmissions of compressed optical samples.

The compressed optical samples are configured to include fewer samples than uncompressed scene optical samples by exploiting compressive sampling. Fewer samples may facilitate utilizing an FOB with a relatively smaller cross section while providing a relatively higher resolution image of the scene. Thus, an image of a scene may be captured and/or transmitted by a relatively smaller imaging system facilitating use in a relatively constrained space.

The FOB 110 is configured to couple the CSO 105 to sensor 115. The sensor 115 may be located a distance from the CSO 105. The FOB 110 is configured to transmit the compressed optical samples from the CSO 105 to the sensor 115. A configuration of the FOEs 112a, ..., 112M in the FOB 110 may be coherent or incoherent. Coherent configurations preserve a location of each FOE 112a, ..., 112M relative to a respective location of each other FOE at an input to the FOB 110 (i.e., at the CSO 105) and an output of the FOB 110 (i.e., at the sensor 115). Incoherent configurations do not preserve the relative locations. Incoherent configurations may further enhance compressive sensing.

The sensor 115 is configured to receive the compressed optical samples and to convert the compressed optical samples into a plurality of electrical samples. The sensor 115 may include a plurality of OSEs 117a, ..., 117P. Each OSE 117a, ..., 117P is configured to capture optical energy, integrate the captured optical energy and to convert the integrated captured optical energy into a respective electrical sample. Each electrical sample corresponds to an integrated intensity of the optical energy incident on a respective OSE 117a, . . . , 117P over an exposure period. Each OSE 117a, . . . , 117P may be understood as a two-dimensional region of the sensor 115 that accepts and integrates incident optical energy. For example, an OSE may be circular or rectangular (e.g., square). An OSE size may correspond to length of a diagonal for a rectangular OSE or a diameter for a circular OSE. For example, OSE sizes may range from about 1 μm to about 12 μm. For example, an image sensor may include a few hundred OSEs to about 21 million OSEs.

In an embodiment, the second end of the FOB 110 may be formed into a rectangular cross section to facilitate coupling the FOB 110 to a rectangular sensor 115. It may be appreciated that a circular FOB 110 coupled to a rectangular sensor 115 may be accommodated by mapping and/or disregarding OSEs that are not receiving optical energy from the FOB 110.

For example, sensor 115 may be an image sensor. OSEs of an image sensor may then correspond to pixels (i.e., picture elements). Image sensors may include CCDs (charge-coupled devices), CIDs (charge injection devices) and CMOS (complementary metal oxide semiconductor) image sensors. For example, CCD and CID image sensors may provide an analog electrical signal output based on received optical energy. Unlike Charge Coupled Device (CCD) image sensors that transfer collected charge out of a pixel during readout (and hence erase the image stored on the sensor), charge does not transfer out of a CID during a read operation. Rather, a displacement current proportional to a charge stored in a pixel is read and the charge remains intact in the pixel after the read operation. Each electrical sample may then be converted to a digital value for processing by post processor 135.

A CMOS image sensor may be configured to provide a digital electrical signal output based on received optical image data. Some CMOS sensors may be configured to allow independent adjustment of integration time and/or gain of each pixel. This functionality may be utilized to compensate for large variations between the intensity of optical samples received by different pixels when viewing a uniform scene (e.g., flat white screen).

In another example, sensor 115 may include a plurality of photodetectors. Each photodetector may be configured to capture a subset of random CSE optical samples and to integrate the subset to produce a compressed optical sample, as described herein. The number of photodetectors corresponds to the number of compressed optical samples utilized for image reconstruction. The photodetectors may be configured to capture infrared optical energy, e.g., optical energy at shortwave infrared wavelengths (1260 nm to 1670 nm). Photodetectors are normally configured to capture visible optical energy (i.e., wavelengths of 400 nm to 1000 nm). Photodetectors may include color filters (e.g. color CCD sensor) or no filters (e.g., broadband monochrome). Monochrome photodetectors used to capture NIR may include a cut filter so that the photodetector receives optical energy in the range of 400 nm to 700 nm. In yet another example, sensor 115 may include a photomultiplier configured to capture relatively low level optical energy such as in Raman and/or fluorescence imaging.

The FOEs 112a, . . . , 112M are configured to carry (i.e., transmit) the compressed optical samples to the sensor 115 and the sensor 115 is configured to convert the compressed optical samples to electrical samples related to the scene 130, as described herein. One or more of FOEs 112a, . . . , 112M may be oriented with respect to sensor 115 so that an OSE 117a, . . . , 117P may receive at least a portion of each of one or more compressed optical samples. As used herein, a sensor optical sample corresponds to the at least a portion of one compressed optical sample. Each OSE 117a, . . . , 117P is configured to integrate received sensor optical samples. Thus, an electrical sample may correspond to at least a portion of each of one or more compressed optical samples. The electrical samples may then be digitized and their associated digital values may be provided to post processor 135.

It is contemplated that integrating sensor optical samples (i.e., at least a portion of each of a plurality of compressed samples) may enhance randomization of optical samples included in a respective electrical sample. It is further contemplated that, for an incoherent FOB, the incoherence represents further randomization. For example, for a compressive sensing imaging system that includes a coherent FOB, compressed samples produced by adjacent FOEs at the first end of the FOB may be incident in adjacent OSEs. Coherence (or incoherence) of scene optical samples included in each compressed optical sample may be generally maintained in the resulting electrical samples. In another example, for a compressive sensing imaging system that includes an incoherent FOB, compressed samples produced by adjacent FOEs at the first end of the FOB may not be incident on adjacent OSEs. Rather, the compressed samples may be incident on random OSEs. Thus, resulting electrical samples may include contributions from further randomized scene portions, i.e., may be more incoherent.

Post processor 135 is configured to receive a plurality of digital values corresponding to electrical samples from sensor 115 and to reconstruct an image of the captured scene based, at least in part on, on the electrical samples. For example, post processor 135 may be configured to implement one or more reconstruction techniques, e.g., convex optimization, basis pursuit, greedy algorithms (e.g., matching pursuit, orthogonal matching pursuit), etc.

Figure 2A:
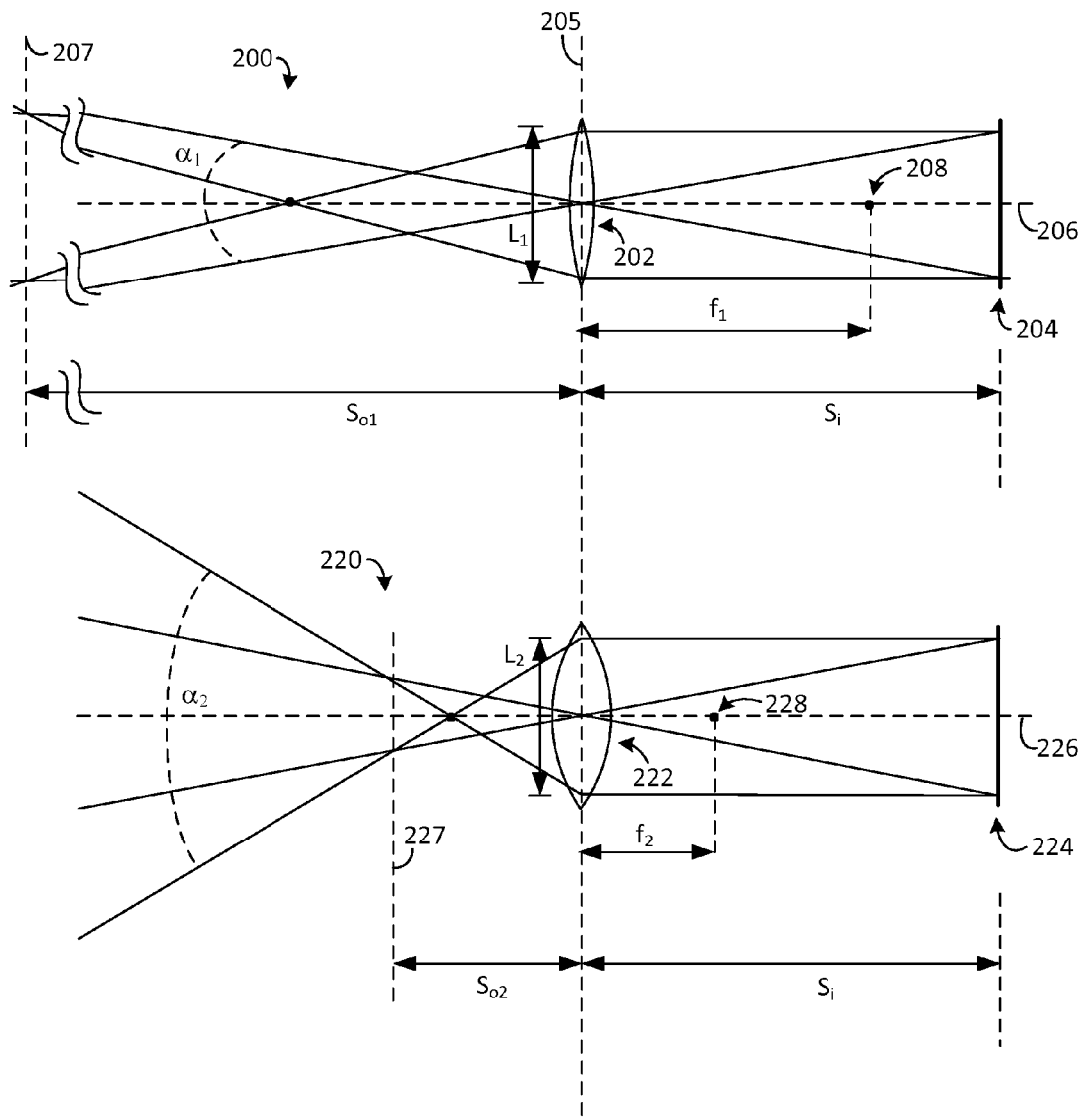
FIG. 2A depicts two example lenses illustrating effects of focal length on size of scene portion captured.

FIG. 2A depicts two example ray diagrams 200, 220 illustrating effects of focal length on size of scene portion captured for two example lens elements 202, 222. Ray diagram 200 includes a relatively longer focal length lens 202 that has a focal point 208 on a lens axis 206 a distance (e.g., focal length) $f_1$ from a lens centerline 205. For example, a focal length of a relatively longer focal length lens may be in the range of about 25 mm (millimeters) to about 200 mm. Lens axis 206 is perpendicular to lens centerline 205 and passes through lens 202 at vertices associated with the lens 202 surfaces. Ray diagram 200 further includes an image plane 204 a distance $S_i$ from the lens centerline 205. For example, the image plane 204 may correspond to at least a portion of a face (i.e., a first end) of an FOE. Ray diagram 200 includes an angle of view, $\alpha_1$, that corresponds to an angular extent of a scene that may be captured by lens 202 and projected onto image plane 204. Angle of view is related to focal length, distance between lens centerline and image plane and size of the image plane. For example, lens 202 may have a relatively long focal length and thus, may have a relatively small angle of view for a given image plane as compared to a lens with a relatively shorter focal length, e.g., lens 222.

Ray diagram 220 includes a relatively shorter focal length lens 222 that has a focal point 228 and a focal length $f_2$. For example, a focal length of a relatively shorter focal length lens may be in the range of about 0.3 mm to about 25 mm. Centerline 205 of lens 202 is also the centerline for lens 222 to facilitate comparison of ray diagrams 200 and 220 and lenses 202 and 222. Ray diagram 220 includes lens axis 226 and image plane 224 positioned a distance $S_i$ from the lens centerline 205. Ray diagram 220 further includes an angle of view $\alpha_2$ and an object plane 227 a distance $S_{o2}$ from lens centerline 205.

As illustrated by ray diagram 220, the relatively shorter focal length lens 222 may have a relatively larger angle of view $\alpha_2$ for a given image plane as compared to a relatively longer focal length lens, e.g., lens 202. Thus, a relatively longer focal length lens may be configured to capture a relatively smaller scene portion. In contrast, a relatively shorter focal length lens may be configured to capture a relatively larger (e.g., wider) scene portion.

In an embodiment, CSO 105 may include one or more concave lenses configured to diverge optical energy. Concave lenses may be configured to distribute scene optical samples over a relatively larger number of FOEs as compared to convex lenses. Similar to convex lenses, e.g., convex lenses 202, 222, a relatively shorter focal length concave lens may diverge optical rays generally more than a relatively longer focal length concave lens may diverge optical rays.

Although 5, is greater than $f_1$ and $f_2$ in example ray diagrams 200, 220, in operation, 5, may be greater than, less than or equal to $f_1$ and/or $f_2$. Further, in operation, image plane(s) 204, 224 may or may not be parallel to centerline 205, i.e., may or may not be perpendicular to lens axis 206, 226. Thus, a plurality of rays from a point in the scene may not project onto a point on an FOE.

Lens 202 has a diameter $L_1$ and lens 222 has a diameter $L_2$. Lens diameters $L_1$, $L_2$ may be related to a diameter of an FOE. In an embodiment, lens diameters $L_1$, $L_2$ may be in the range of one quarter of an FOE diameter to equivalent to an FOE diameter. In another embodiment, lens diameters $L_1$, $L_2$ may be in the range of equivalent to an FOE diameter to three times an FOE diameter. For example, lens diameters may be in the range of 10 μm to 75 μm. A number of scene optical samples accepted by an FOE may be related to a lens diameter (and FOE diameter).

A size of a coverage area (i.e., an area of an image plane that receives optical energy from a lens) may be related to lens diameter, distance 5, and/or an angle of the image plane (i.e., first end of an FOE) relative to the lens centerline. The coverage area is related to lens focal length. For example, a relatively long focal length lens, e.g., lens 202, may correspond to a relatively smaller coverage area and a relatively shorter focal length lens, e.g., lens 222, may correspond to a relatively larger coverage area.

Figure 2B:
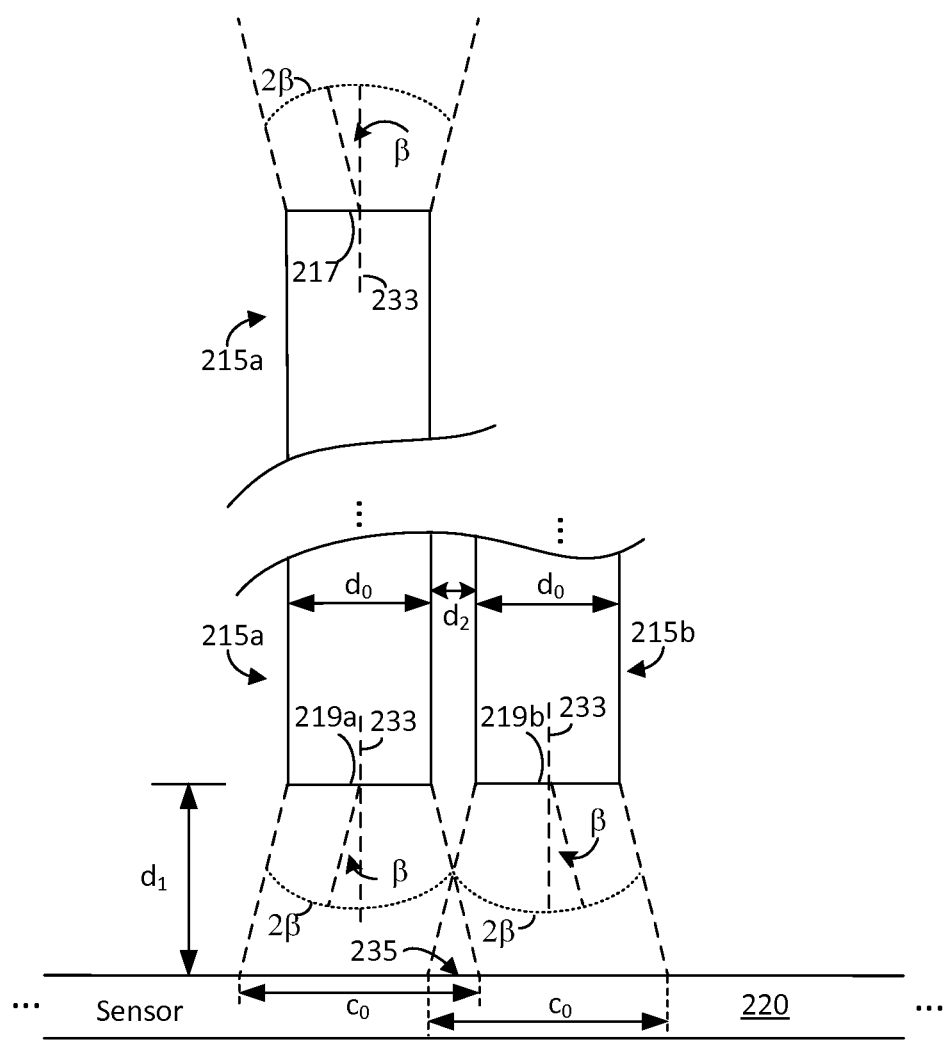
FIG. 2B illustrates fiber optic element acceptance angle and interface of fiber optic elements to a sensor.

FIG. 2B illustrates an FOE acceptance (and/or emission) angle β and interface of FOE 215a and a portion of an FOE 215b to a sensor 220. FOE 215a and FOE 215b are examples of FOEs 112a, . . . , 112M and sensor 220 is an example of sensor 115 of FIG. 1. FOE 215a includes a first end 217 and a second end 219a. FOE 215b includes a second end 219b. A sensor 220 may be positioned relative to the second ends 219a, 219b. Optical parameters associated with FOEs 215a, 215b may affect capture of optical energy (e.g., scene optical samples) by the FOEs 215a, 215b. For example, FOEs 215a, 215b have an associated acceptance cone. Acceptance cone is related to an acceptance angle, e.g., angle β, that is related to a numerical aperture of the optical fiber elements 215a, 215b. The acceptance angle β corresponds to a maximum angle with respect to a fiber axis 233 of an incident ray that may be accepted by the FOEs 215a, 215b. In other words, an incident ray at an angle greater than β with respect to the FOE axis 233 may reach the FOE 215a at first end 217 but may not be accepted, i.e., may be reflected. The acceptance cone bounds a volume with respect to a first end of an FOE, e.g., FOE 215a, 215b where an incident ray may be accepted by the FOEs 215a, 215b. The acceptance cone is bounded by a full acceptance angle that is twice the acceptance angle, i.e., 2β. Only a portion or all of a CSE optical sample delivered by the CSO whose rays are within the acceptance cone and whose ray angles with respect to the fiber axis are within the acceptance angle may be integrated into the compressed optical sample conveyed by the FOE.

The numerical aperture of the FOEs 215a, 215b represents a size or degree of openness of the acceptance cone. The FOEs 215a, 215b may include a fiber core that may be coated with a cladding material. The numerical aperture ("N.A.") of an FOE is defined as:

$$N.A. = \frac{\sqrt{n_1^2 - n_2^2}}{n}$$

where $n_1$ is the refractive index of the fiber core, $n_2$ is the refractive index of the fiber cladding and n is the refractive index of the medium that the FOE is in. Refractive index is a ratio of a speed of light in a vacuum to a speed of light in a medium, e.g., fiber core. The refractive index for air is approximately 1.00. For an FOE in air, without cladding, $n_2$ may equal the refractive index of air, i.e., approx. 1.00. The acceptance angle, β, of the FOE is then the arcsine of the numerical aperture, i.e., $$\beta = \sin^{-1}\left(\frac{\sqrt{n_1^2 - n_2^2}}{n}\right).$$

An FOE may act as an optical waveguide, i.e., may guide optical energy received at a first end, e.g., first end 217, along its length to a second end, e.g., second end 219a. An FOE may propagate optical energy, e.g., a compressed optical sample, that results from at least portions of CSE optical samples that arrive within the acceptance cone and within the acceptance angle of the FOE. Compressed optical sample(s) may then propagate along the FOE(s) by internal reflection at an interface between the fiber core and cladding or air.

An FOE may emit optical energy from its second end 219a, 219b in an output cone (i.e., emission cone). Similar to the acceptance cone of the first end 217, the output cone may be defined by a solid angle, 2β (emission angle), related to the numerical aperture of the fiber. The second ends 219a, 219b of FOEs 215a, 215b may be positioned relative to sensor 220. The second ends 219a, 219b may be further positioned relative to each other in their associated FOB. A compressed optical sample that is produced by FOE 215a from accepted scene optical sample(s) may propagate along FOE 215a to the second end 219a. Optical energy (i.e., intensity) associated with the compressed optical sample may be emitted from the second end 219a within the output cone defined by solid angle 2β. The acceptance angle β, FOE diameter $d_0$ and a distance $d_1$ between the second end 219a of the FOE and a surface of the sensor 220 may define a coverage area (e.g., circle of diameter $c_0$) of the sensor 220 associated with FOE 215a. The coverage area may receive the compressed optical samples. The acceptance angle β and distance $d_1$ to surface of the sensor 220 may be related to an amount of optical coupling between the FOE 215a and the sensor 220. The coverage area may include a portion of an OSE, up to a plurality of OSEs.

Relative positions of FOE 215a and FOE 215b may affect coverage area and mapping of compressed optical samples to sensor 220. For example, FOE 215a may be separated from adjacent FOE 215b by a distance $d_2$. Distance $d_2$ is generally less than FOE diameter $d_0$ and may be related to FOB manufacturing process. For example, $d_2$ may be in the range of zero to $d_0/2$. Adjacent FOEs touching corresponds to $d_2=0$. Thus, for a rectangular packing arrangement, $d_2=0$ for FOEs adjacent in an x direction and y direction for a fiber axis parallel to a z direction (in an x,y,z coordinate system). Diagonally adjacent FOEs may be separated by $\sqrt{2}d_0-d_0 \cong 0.414d_0$. For a triangular packing arrangement, $d_2=0$ for adjacent FOEs. It may be appreciated that a relatively well-packed FOB may include space among the FOEs. For example, a packing fraction may be on the order of 82% for a well-packed FOB.

Coverage area and diameter $c_0$ may decrease as distance $d_1$ decreases and coverage area and diameter $c_0$ may increase as distance $d_1$ increases. For example, distance $d_1$ may be in the range of zero to three times FOE diameter. When $d_1$ is at or near zero, coverage areas associated with FOEs 215a and 215b may not overlap. A diameter $c_0$ of each coverage area may then correspond to FOE diameter $d_0$. When $d_1$ is greater than zero, an OSE of sensor 220 may receive a portion of the optical energy from adjacent FOEs. As $d_1$ is increased, the individual coverage areas may overlap 235. An amount of overlap 235 may be related to $d_1$, $d_2$ and/or $\beta$. Overlap 235 may further randomize and/or integrate sensor optical samples, as described herein.

Thus, a plurality of FOEs, including, e.g., FOEs 215a, 215b, may accept one or more scene optical samples at a first end, e.g., first end 217, to integrate accepted scene optical samples to produce a compressed optical sample, to carry (i.e., transmit) the compressed optical sample to a second end, e.g., second ends 219a, 219b and to emit the compressed optical sample in an emission cone. At least a portion of the compressed optical sample (i.e., sensor optical sample) may be received by one or more OSEs associated with a sensor, e.g., sensor 220.

Figure 3A:
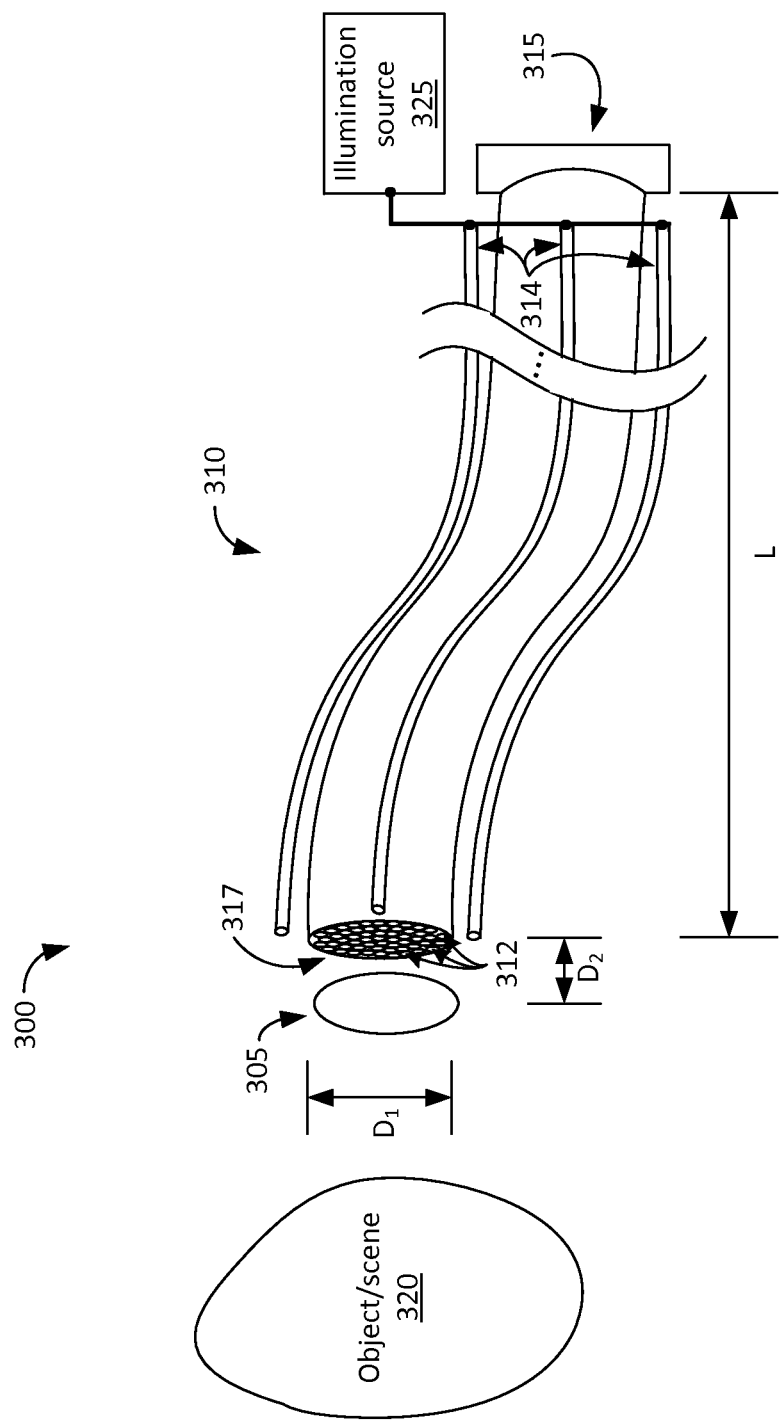
FIG. 3A is a sketch of one example of a compressive sensing imaging system consistent with the present disclosure.

FIG. 3A is a sketch of one example of a compressive sensing imaging system 300 consistent with the present disclosure. Compressive sensing imaging system 300 is one example of compressive sensing imaging system 100 of FIG. 1. The compressive sensing imaging system 300 includes a CSO 305, an FOB 310 and a sensor 315 and is configured to compressively sample scene 320. The FOB 310 has a diameter $D_1$ and a length L and is configured to integrate accepted scene optical samples and to couple the CSO 305 to the sensor 315. The FOB 310 includes a plurality of FOEs 312. The FOB 310 includes a first end 317 and CSO 305 may be positioned a distance $D_2$ from the first end 317. For example, $D_2$ may be in the range of zero to $3*D_1$. For example, for a random mirror CSO, $D_2$ may be at or near $3*D_1$. Example compressive sensing system 300 may include an illumination source 325 and one or more illumination fiber(s) 314 configured to illuminate scene 320.

CSO 305 may include a random lens, a microlens array, a diffraction grating, and/or a diffractive optic. The CSO 305 is configured to capture a plurality of random CSE optical samples of a scene 320 (that may include an object) and to provide the plurality of CSE optical samples to the FOB 310. Each CSE optical sample corresponds to a portion of the scene captured by a respective CSE 312 included in CSO 305 and each CSE optical sample includes optical energy (e.g., light intensity) associated with the respective scene portion. Each FOE 312 is configured to accept scene optical samples (i.e., at least a portion of the CSE optical samples that are within an associated acceptance cone and acceptance angle). Each FOE 312 is further configured to integrate the scene optical samples to produce a compressed optical sample and transmit the compressed optical sample to the sensor 315.

Figure 3B:
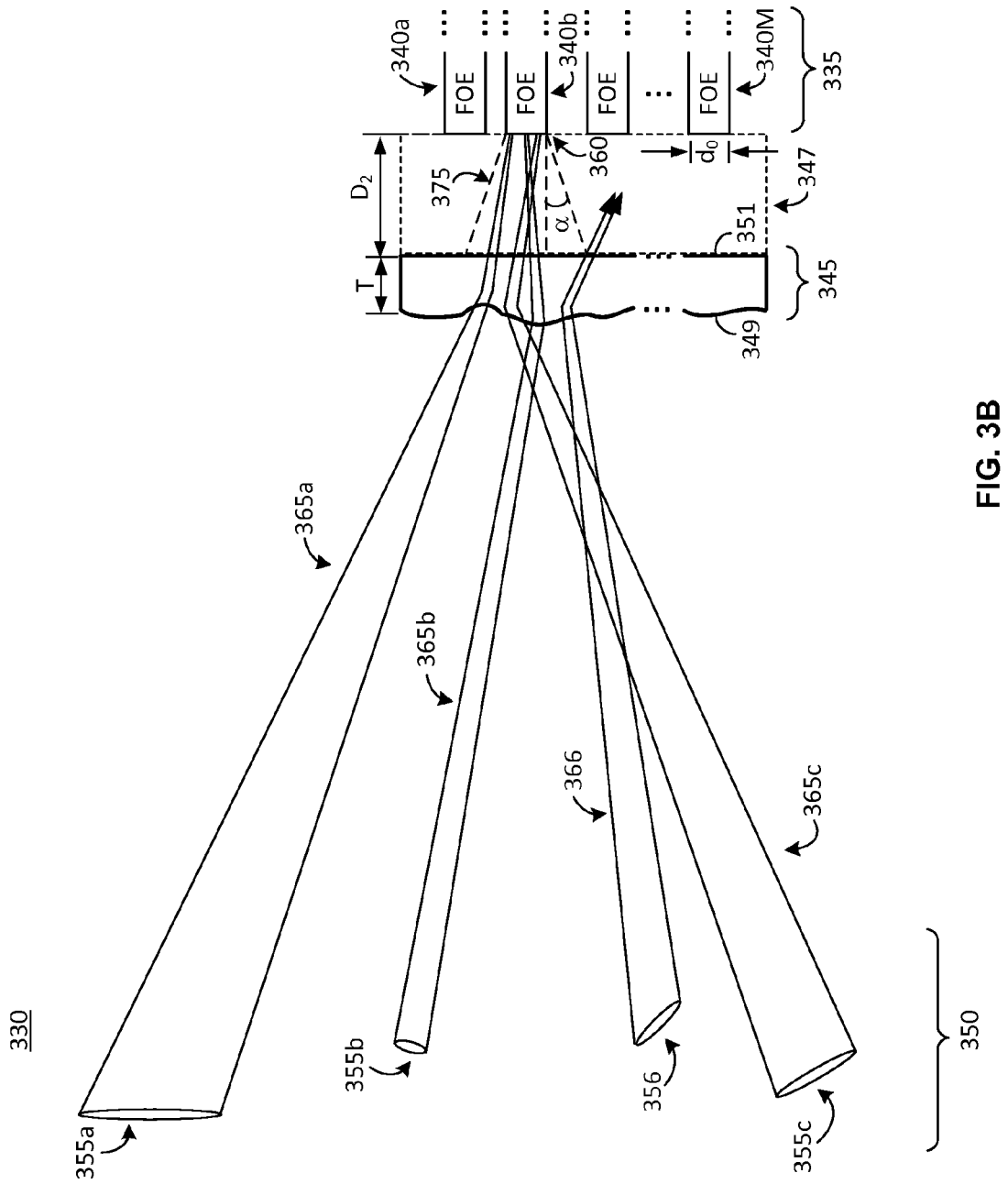
FIG. 3B is a sketch of an example mapping of a plurality of scene optical samples onto an FOE.

FIG. 3B is a sketch 330 of an example mapping of a plurality of CSE optical samples onto an FOE. It may be appreciated that sketch 330 is not drawn to scale and is configured to illustrate mapping a plurality of random scene portions onto one FOE. Sketch 330 is thus simplified for ease of illustration, may include fewer than all the components of a compressive sensing imaging system and is configured to illustrate one example of mapping.

Sketch 330 includes an FOB 335 that includes a plurality of FOEs 340a, 340b, . . . , 340M, a CSO 345 and a scene 350. In this example 330, a plurality of scene portions 355a, . . . , 355c are mapped onto a first end 360 of FOE 340b by CSO 345. For example, CSO 345 may include a random lens and/or microlens array that includes a plurality of randomly positioned and/or oriented microlenses (i.e., CSEs). CSO 345 includes a first surface 349 and a second opposing surface 351 and has a nominal thickness T between the first surface 349 and the second surface 351. For example, the thickness T may be in the range of about 0.5 mm to about 2 mm. The first surface 349 may correspond to a plurality of CSE first surfaces, e.g., microlens surfaces. The second surface 351 may correspond to a surface of a substrate and/or may correspond to the plurality of second surfaces of the CSEs. CSO 345 is positioned a distance $D_2$ (measured from the second surface 351) from the FOB 335, i.e., a distance $D_2$ from the first end 360. The value of $D_2$ may be related to FOE diameter $d_0$, as described herein. The region between CSO 345 and FOB portion 335 may include a coupling 347 and/or coupling material configured to interface CSO 345 with FOB 335.

CSO 345 is configured to capture a plurality of CSE optical samples corresponding to the plurality of scene portions 355a, . . . , 355c. Optical energy associated with each scene portion is illustrated as an associated ray field, e.g., ray fields 365a, . . . , 365c. Each ray field 365a, . . . , 365c may thus correspond to a respective CSE optical sample, e.g., 355a, . . . , 355c. Each ray field 365a, . . . , 365c may be incident on the first surface 349 of CSO 345 and may be refracted by one or more associated CSEs. The refracted ray fields may then be incident on a first surface of one or more FOEs, e.g., first surface 360 of FOE 340b.

FOE 340b has an associated acceptance angle $\alpha$ and an associated acceptance cone 375 that has a full acceptance angle of $2\alpha$. FOE 340b is configured to accept rays (associated with optical scene portions) that are within the acceptance cone 375 and whose angles of incidence relative to the FOE 340b axis are less than or equal to the acceptance angle $\alpha$. Rays within the acceptance cone whose angles of incidence are greater than the acceptance angle $\alpha$ may be reflected. Whether a ray is accepted by FOE 340b may be related to a geometry of first end 360. For example, a convex-shaped first end may refract an incident ray to reduce its angle with respect to the fiber axis. Thus, a ray approaching FOE 340b at an angle greater than its acceptance angle may be refracted and accepted providing a relatively larger range of incident angles that may be accepted compared to a generally flat first end 360. In this example 330, acceptance angle 375 corresponds to a generally flat first end 360. Ray fields 365a, . . . , 365c are within acceptance cone 375 and acceptance angle $\alpha$. Ray field 366 associated with scene portion 356 is not within the acceptance cone 375 and thus, is not received by FOE 340b.

Distance $D_2$ may affect distribution of captured ray fields across FOEs 340a, 340b, . . . , 340M. For example, if $D_2$ is at or near zero, generally only rays that exit the second surface 351 at an area corresponding to an area of the first end 360 of FOE 340b may be accepted by FOE 340b. Further, such rays may generally be incident only on FOE 340b and not on other adjacent FOEs in FOB 335. In another example, if $D_2$ is greater than zero then rays that exit the second surface 351 of CSO 345 may exit from a relatively larger area and still be received by FOE 340b at least in part due to a size of a cross section of the acceptance cone at second surface 351. Continuing with this example, portions of ray fields exiting the second surface 351 may also be incident on a plurality of the FOEs. Thus, optical energy associated with one scene portion may be distributed across more than one FOE. When $D_2 > 0$, FOEs are better able to integrate multiple scene optical samples because a greater portion of the CSO 345 lies within the acceptance cone of each FOE 340a, 340b, ..., 340M.

CSO 345 is configured to capture CSE optical samples and to direct/guide the optical energy 365a, ..., 365c to the first end 360 of FOE 340b. The scene portions 355a, ..., 355c associated with the corresponding CSE optical samples may be relatively widely distributed in scene 350. The associated CSE optical samples 365a, ..., 365c have been randomly refracted by CSO 345 so spatial separation and/or relative positioning may not be preserved. Accordingly, CSE optical samples corresponding to randomly positioned scene portions may be captured by CSO 345 and at least a portion of each CSE optical sample of a respective subset of random CSE optical samples may be provided to each FOE 340a, 340b, ..., 340M. Each FOE 340a, 340b, ..., 340M is configured to integrate respective accepted scene optical samples to produce a respective compressed optical sample. Each accepted scene optical sample corresponds to at least a portion of a CSE optical sample, as described herein. Thus, each compressed optical sample may include contributions from a plurality of random scene portions.

A relative size of each scene portion associated with a respective CSE optical sample may not be uniform. For example, the size of the scene portion associated with the CSE optical sample may be related to lens geometry of a lens that captured the CSE optical sample. A lens with a relatively greater focal length may correspond to capture of a relatively smaller portion of the scene. A lens with a relatively shorter focal length may correspond to capture of a relatively larger portion of the scene. Thus, a CSO, e.g., CSO 345, may be configured to include optical elements with varying focal lengths to enhance randomly sampling the scene. In other words, random sampling may be enhanced through variation of the size of each scene portion captured.

For ease of illustration, example 330 illustrates one subset of CSE optical samples 365a, ..., 365c that are captured by CSO 345 and provided to FOE 340b. CSO 345 is configured to provide a respective subset of scene optical samples to each FOE 340a, 340b, ..., 340M. Each subset may be similarly random. Further, example 330 illustrates CSE optical samples that are provided to one FOE. CSO 345 may be configured to provide a portion of one or more CSE optical samples to a plurality of FOEs, as described herein.

Thus, CSO 345 may be configured to capture a plurality of random CSE optical samples and to provide subsets of CSE optical samples to FOEs 340a, 340b, ..., 340M. Each CSE optical sample corresponds to a respective scene portion. Each FOE 340a, 340b, ..., 340M is configured to integrate accepted scene optical samples to produce a respective compressed optical sample. The compressed optical sample may correspond to a combination, e.g., a sum, of at least a portion of each of the random scene optical samples. Selection of the scene optical samples included in a combination may be related to scene geometry, CSO 345 characteristics, first end 360 characteristics (e.g., geometry) and/or spatial relationships between CSO 345, FOB 335 (and FOEs 340a, 340b, ..., 340M) and scene 350.

Figure 4A:
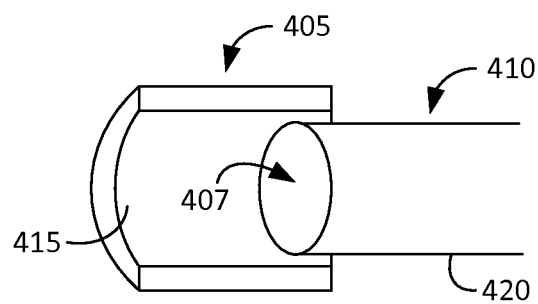
FIGS. 4A and 4B depict two examples of random minor compressive sensing optics consistent with the present disclosure.
Figure 4B:
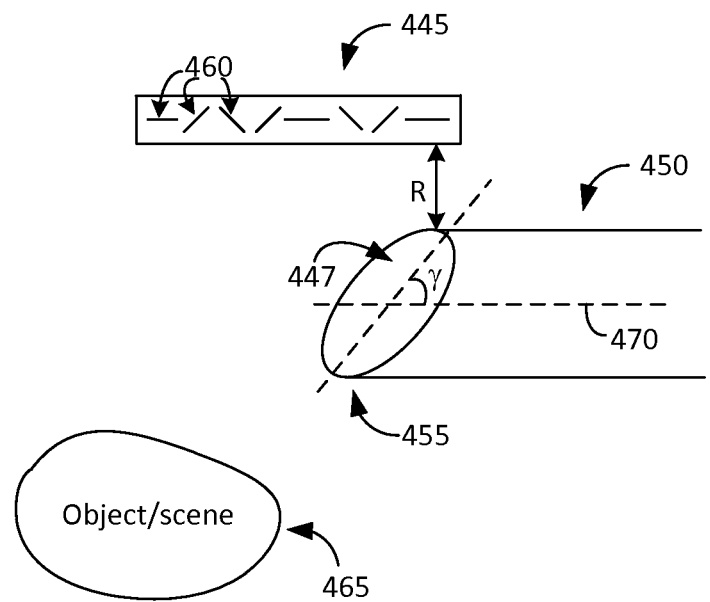

Attention is directed to FIGS. 4A and 4B that depict two examples of random minor CSOs 405, 445 consistent with the present disclosure. Random mirrors 405, 445 are configured to facilitate capturing CSE optical samples when an FOB 410, 450 (i.e., an axis of the FOB) is not aligned with the scene to be imaged.

Turning now to FIG. 4A, a shape of random mirror 405 is generally curved approximating an inner radial surface 415 of a portion of a cylinder. Random mirror 405 is positioned so that a portion of the inner radial surface 415 is adjacent an outer radial surface 420 of FOB 410. Random mirror 405 may include a plurality of randomly positioned and/or randomly oriented reflective elements configured to reflect ray fields associated with scene portions and CSE optical samples from a scene to FOB 410. In some embodiments, a micro lens array 407 may be coupled to or formed on a first end of FOB 410, configured to facilitate capture of scene optical samples from random minor 405. The microlens array 407 may be configured to further randomize the CSE optical samples prior to provision to FOE(s) for integration and transmission to a sensor.

Turning now to FIG. 4B, random mirror 445 may be generally rectangular shaped and is positioned adjacent a first end 455 of FOB 450 a radial distance R from the FOB 450. Random mirror 445 may include a plurality of randomly positioned reflective elements 460 configured to capture (i.e., reflect) CSE optical samples corresponding to respective scene portions from a scene 465 to FOB 450. A micro lens array 447 may be coupled to or formed on the first end 455 of FOB 450, configured to facilitate capture of the optical image data. In this example, a surface of the first end of FOB 450 may be oriented at an angle, γ, relative to an axis 470 of FOB 450 to facilitate capturing reflected optical image data from random mirror 445.

Thus, random mirrors may be used to capture random CSE optical samples when the scene is not aligned with the FOB. The CSE optical samples may be reflected onto FOEs included in FOB 410, 450. Respective subsets of random scene optical samples may be integrated by each FOE to form a respective compressed optical sample that may then be transmitted to a sensor, as described herein.

Figure 5A:
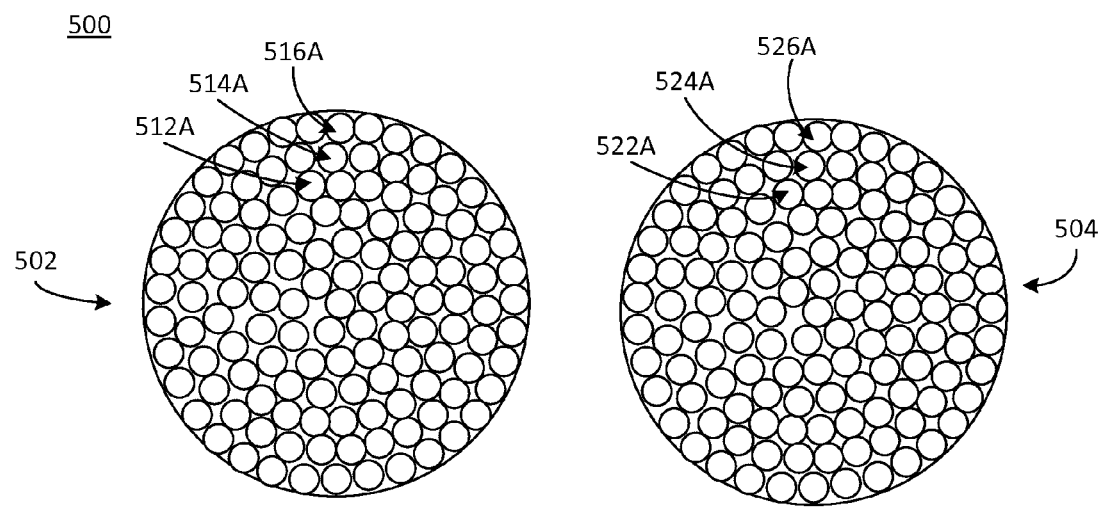
FIGS. 5A and 5B depict an example of a coherent optical fiber bundle and an example of an incoherent optical fiber bundle, respectively.
Figure 5B:
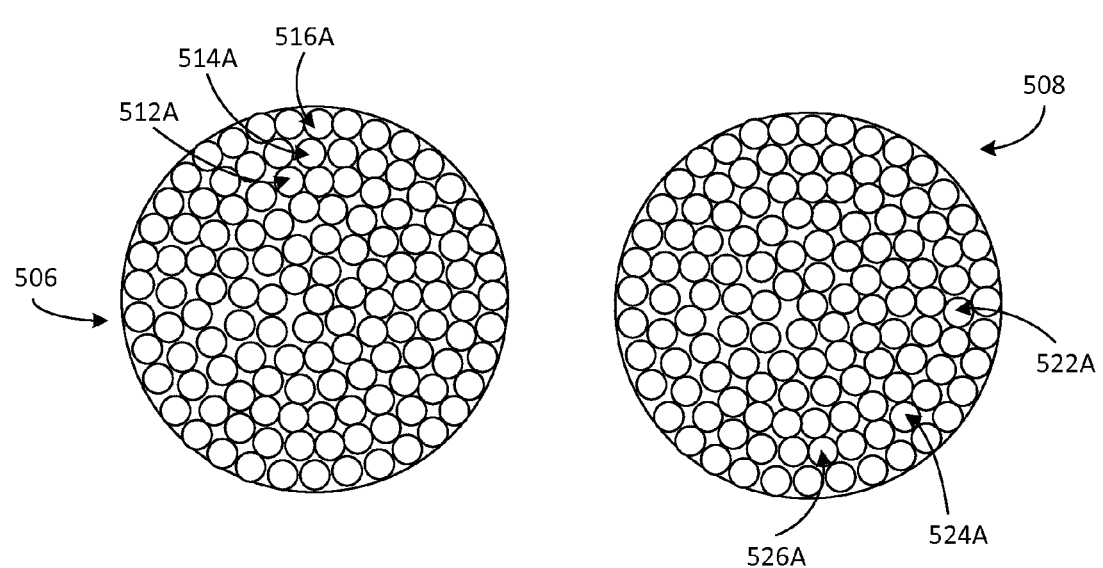

Attention is directed to FIGS. 5A and 5B that depict an example 500 of a coherent FOB and an example 505 of an incoherent FOB, respectively. In both examples 500, 505, first end 512A and second end 522A are respective ends of a first FOE, first end 514A and second end 524A are respective ends of a second FOE and first end 516A and second end 526A are respective ends of a third FOE. Coherent FOB 500 includes a first end 502 and a second end 504. In coherent FOB 500, relative positions of FOEs at the first end 502 are preserved at the second end 504. Thus, the relative positions of first ends 512A, 514A and 516A correspond to the relative positions of second ends 522A, 524A and 526A. Incoherent FOB 505 includes a first end 506 and a second end 508. In incoherent FOB 505, relative positions of FOEs at the first end 506 may not be preserved at the second end 508. In this example 505, the relative positions of first ends 512A, 514A and 516A do not correspond to the relative positions of second ends 522A, 524A and 526A.

An incoherent FOB, e.g., FOB 505, with a random mapping between FOEs at the first end 506 and the second end 508 may facilitate compressive sampling. Although incoherence may be provided by a CSO, incoherent FOE mapping may support relatively greater incoherence of the compressed optical samples that are provided to a sensor, as described herein. It may be appreciated that a relatively lesser degree of incoherence may be provided by FOBs that are not specifically incoherent, i.e., relative positions of FOEs may not be controlled and/or may not be randomized during manufacturing. Such FOBs may typically be used for illumination applications and may be relatively low cost as compared to coherent FOBs typically used for imaging applications.

Figure 6:
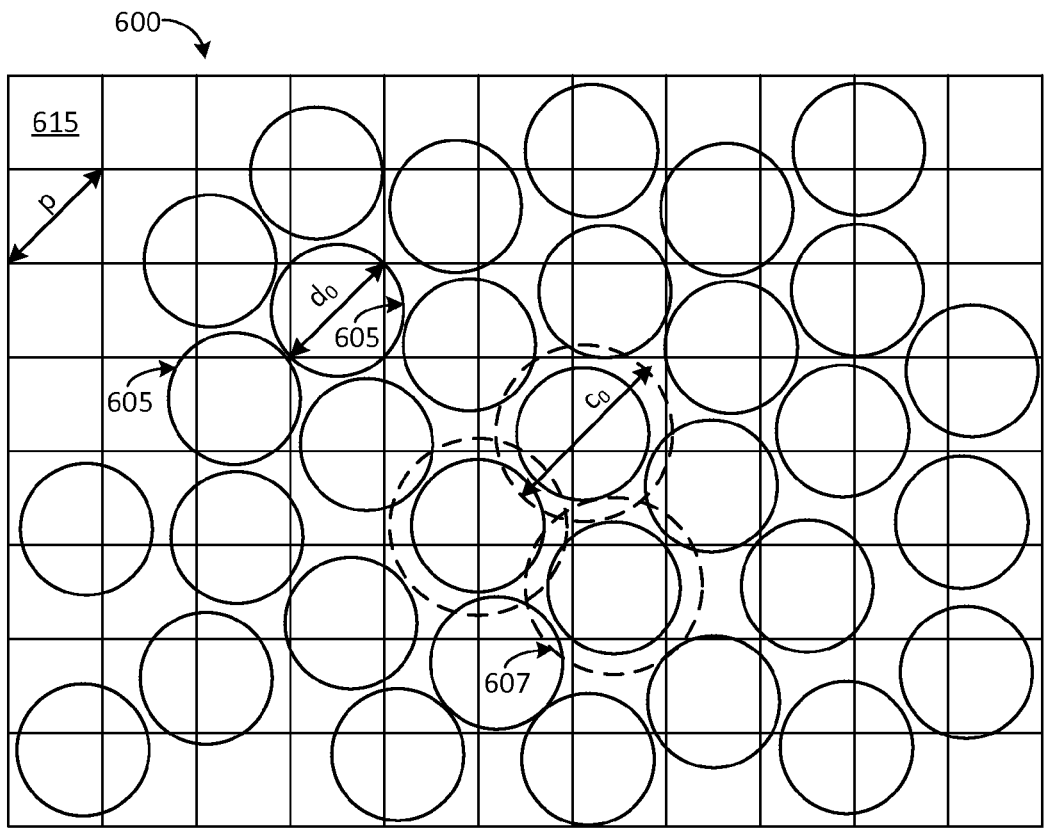
FIG. 6 depicts an example distribution of fiber optic elements on a sensor.

Attention is directed to FIG. 6 depicting an example of distribution of FOEs coupled to a portion of a sensor 600. In this illustrative example, sensor 600 may correspond to an image sensor and thus OSEs may correspond to pixels. It may be appreciated that various other FOE distributions may be implemented, within the scope of this disclosure. In FIG. 6, solid circles correspond to FOE cross-sectional area, dotted circles correspond to acceptance cone cross sections at the sensor surface and squares correspond to pixels. Other pixel shapes (e.g., rectangles) may be implemented within the scope of the present disclosure.

The image sensor portion 600 includes a plurality of pixels, e.g., pixel 615. A plurality of FOEs, e.g., FOE 605, may be distributed over the image sensor portion 600. In this example, a diameter, $d_0$, of an FOE 605 corresponds to a diagonal, p, of a pixel 615. It may be appreciated that $d_0$ may be greater than or less than p, within the scope of the present disclosure. Each FOE 605 may further include an acceptance (i.e., emission) cone 607 with diameter $c_0$, $c_0$ greater than or equal to $d_0$. The diameter $c_0$ may be related to a distance between a FOB and sensor surface, as illustrated in FIG. 2B. Increasing the distance between a first end of an FOB (and/or FOE) and sensor surface corresponds to an increase in cone diameter $c_0$. Due to packing characteristics, FOEs 605 may be positioned at random (relatively small) distances from adjacent FOEs. Further, sensors may also be characterized by a fill factor. Fill factor is the percentage of a sensor surface that is sensitive to light. In other words, adjacent pixels may be separated by non-light sensitive regions. Distribution of FOEs 605 may not correspond to the distribution of pixels. For example, a first FOE may illuminate a portion of one or more pixels and a second FOE may illuminate different portions of a different number of pixels.

Each FOE 605 may be configured to emit optical energy associated with a respective compressed optical sample and to illuminate a portion of the surface of sensor 600 that is included in a respective emission cone 607. The portion of the surface of the sensor may include respective portions of one or more pixels. Each FOE may illuminate a respective portion of each of a plurality of adjacent pixels. Each FOE may be configured to illuminate a portion of each of a number of pixels. The number of pixels may be related to FOE diameter, pixel size, distance between FOE and sensor surface, acceptance (i.e. emission) cone of FOE and/or separation of pixels.

Each pixel may be configured to receive a portion of a compressed optical sample (i.e., a sensor optical sample) from one or more FOEs. Each pixel may be configured to receive sensor optical samples from a number of FOEs. The number of FOEs may be related to FOE diameter, pixel size, distance between FOE and sensor surface, acceptance (i.e. emissions) cones of FOEs and/or separation of FOEs. Thus, the mapping of compressed optical sample energy from a plurality of FOEs onto a plurality of pixels may be pseudo-random. The mapping may be adjusted by moving the FOB in a lateral direction relative to the surface of the sensor. Thus, sensor optical samples may be integrated and/or randomized at the FOB/sensor interface.

Figure 7:
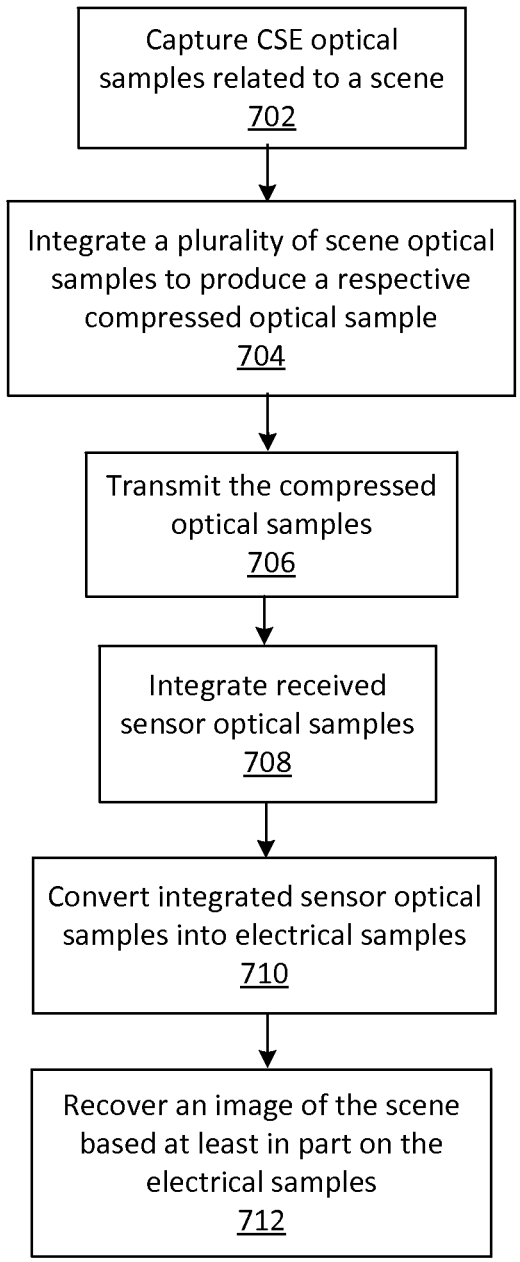
FIG. 7 depicts an exemplary flow chart of operations consistent with the present disclosure.

Attention is directed to FIG. 7 which is an example flow chart 700 for compressive sampling using an apparatus and/or system consistent with the present disclosure. Program flow may begin with capturing CSE optical samples related to a scene at operation 702. For example, the CSE optical samples may be captured by a CSO that includes a plurality of CSEs. A plurality of scene optical samples may be integrated to produce a respective compressed optical sample at operation 704. For example, an FOE may be configured to receive the scene optical samples (i.e., at least a portion of each of a plurality of CSE optical samples) from the CSO and to integrate the scene optical samples to produce the compressed optical sample. The compressed optical samples may be transmitted at operation 706. Received sensor optical samples may be integrated at operation 708. For example, each OSE of a sensor may be configured to receive at least a portion of each of a plurality of compressed optical samples (i.e., sensor optical samples) and to integrate the received sensor optical samples. Integrated sensor optical samples may be converted into electrical samples at operation 710. For example, the sensor may be configured to convert the integrated sensor optical samples into electrical samples. An image of the scene may be recovered, based at least in part, on the electrical samples at operation 712. For example, the image of the scene may be recovered by digitizing the electrical samples and processing the corresponding digital values according to a reconstruction technique.

Accordingly, a compressive sensing imaging system, apparatus and/or method, consistent with the present disclosure is configured to facilitate imaging a scene that may include an object. A CSO that includes a plurality of CSEs is configured to capture random CSE optical samples and to provide the CSE optical samples to an FOB. Each CSE optical sample corresponds to a portion of the scene. The FOB includes a plurality of FOEs. Each FOE is configured to receive a respective subset of scene optical samples and to integrate the scene optical samples to produce a respective compressed optical sample. Each scene optical sample corresponds to at least a portion of a CSE optical sample. A plurality of compressed optical samples may be produced in parallel. The FOB is configured to transmit the compressed optical samples from the CSO to a sensor remote from the CSO. A configuration of the FOEs in the FOB may be coherent or incoherent. The sensor is configured to receive the compressed optical samples. Each OSE is configured to capture and integrate at least a portion (i.e., a sensor optical sample) of each of a plurality of compressed optical samples and to convert the sensor optical samples into electrical samples. The electrical samples may then be digitized and processed by a post processor to recover a representation of the scene and/or the object.

The compressed optical samples are configured to include fewer samples than uncompressed scene optical samples by exploiting compressive sampling. Fewer samples may facilitate utilizing an FOB with a relatively smaller cross section while providing a relatively higher resolution image of the scene. Thus, an image of a scene may be captured and/or transmitted by a relatively smaller imaging system facilitating use in a relatively constrained space.

Figure 8:
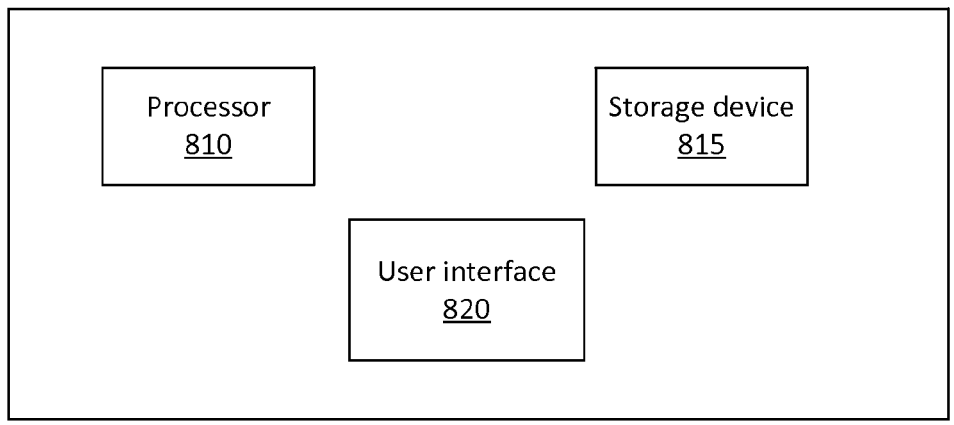
FIG. 8 illustrates an example of a processing system that contains a processor, a storage device and a user interface.

It should also be appreciated that some of the functionality described herein for the embodiments of the present invention may be implemented by using hardware, software, or a combination of hardware and software, as desired. If implemented by software, a processor and a storage device are required. The processor may be any type of processor capable of providing the speed and functionality required by the embodiments of the invention. The storage device may include any type of tangible, non-transitory storage device capable of storing instructions adapted to be executed by a processor. Some examples of such storage devices include, but are not limited to, read-only memory (ROM), random-access memory (RAM), programmable ROM (PROM), erasable programmable ROM (EPROM), electronically erasable programmable ROM (EEPROM), dynamic RAM (DRAM), magnetic disk (e.g., floppy disk and hard drive), optical disk (e.g. CD-ROM), and any other device that can store digital information. The instructions may be stored on a device in a compressed and/or encrypted format. Accordingly, in the broad context of the present invention, and with attention to FIG. 8, compressive sensing imaging system may include a processor (810), a storage device (815) and user interface (820).

Although illustrative embodiments and methods have been shown and described, a wide range of modifications, changes, and substitutions is contemplated in the foregoing disclosure and in some instances some features of the embodiments or steps of the method may be employed without a corresponding use of other features or steps. Accordingly, it is appropriate that the claims be construed broadly and in a manner consistent with the scope of the embodiments disclosed herein.

What is claimed is:

1. A compressive sensing apparatus comprising:
   a compressive sensing optic (CSO) comprising a plurality of compressive sensing elements (CSEs), each CSE configured to capture a respective random CSE optical sample, each CSE optical sample related to a respective portion of a scene; and
   a fiber optic bundle (FOB) coupled to the CSO at a first end of the FOB, the FOB comprising a number of fiber optic elements (FOEs), each FOE configured to integrate one or more accepted scene optical samples to produce an associated compressed optical sample, each scene optical sample corresponding to at least a portion of a respective CSE optical sample,
   wherein each CSE is configured to provide the respective CSE optical sample to the FOB and each FOE is configured to carry the associated compressed optical sample from the first end to a second end of the FOB configured to be coupled to a sensor.

2. The apparatus of claim 1 wherein the CSO comprises at least one of a lens, a mirror, a microlens array, a micromirror array and a diffractive optical element.

3. The apparatus of claim 1 wherein the FOB is incoherent so that relative positions of at least some of the FOEs at the first end of the FOB are different from relative positions of the at least some FOEs at the second end of the FOB.

4. The apparatus of claim 1 wherein the CSEs are lens elements and a diameter of each lens element is one quarter to one diameter of each FOE.

5. The apparatus of claim 1 wherein the diameter of each FOE is 10 μm (micrometers).

6. The apparatus of claim 1 wherein the CSO comprises a plurality of random mirrors and the CSO is positioned a radial distance from the FOB.

7. The apparatus of claim 1 wherein the CSO is formed on the first end of the FOB so that a first end of each FOE corresponds to a respective CSE.

8. A system comprising:
   a compressive sensing optic (CSO) comprising a plurality of compressive sensing elements (CSEs), each CSE configured to capture a respective random CSE optical sample, each CSE optical sample related to a respective portion of a scene;
   a fiber optic bundle (FOB) coupled to the CSO at a first end of the FOB, the FOB comprising a number of fiber optic elements (FOEs), each FOE configured to integrate one or more accepted scene optical samples to produce an associated compressed optical sample, each scene optical sample corresponding to at least a portion of a respective CSE optical sample; and
   a sensor coupled to a second end of the FOB, the sensor comprising a plurality of optical sensing elements (OSEs), each OSE configured to integrate one or more received sensor optical samples,
   wherein each CSE is configured to provide the respective CSE optical sample to the FOB, each FOE is configured to provide the associated compressed optical sample to the sensor and each sensor optical sample corresponds to at least a portion of a respective compressed optical sample.

9. The system of claim 8 wherein the sensor is further configured to convert the integrated sensor optical samples into electrical samples and further comprising a post processor configured to recover an image of the scene based, at least in part, on the electrical samples.

10. The system of claim 8 further comprising:
    an illumination fiber configured to illuminate the scene.

11. The system of claim 10 wherein the illumination fiber is configured to provide at least one of infrared optical energy, ultraviolet optical energy and visible light to the scene.

12. The system of claim 8 wherein the CSO comprises at least one of a lens, a minor, a microlens array, a micromirror array and a pattern diffraction grating.

13. The system of claim 8 wherein the FOB is incoherent so that relative positions of at least some of the FOEs at the first end of the FOB are different from relative positions of the at least some FOEs at the second end of the FOB.

14. The system of claim 8 wherein the sensor is an image sensor comprising a plurality of pixels and a diagonal dimension of each pixel is related to a diameter of each FOE.

15. The system of claim 8 wherein the CSEs are lens elements and a diameter of each lens element is one quarter to one diameter of each FOE.

16. A method comprising:
    capturing, by each compressive sensing element (CSE) of a plurality of CSEs in a compressive sensing optic (CSO), a respective random CSE optical sample related to a respective portion of a scene;
    providing, by each CSE, the respective CSE optical sample to a fiber optic bundle (FOB) comprising a plurality of fiber optic elements (FOEs); and
    integrating, by each FOE, one or more accepted scene optical samples to produce an associated compressed optical sample, wherein each scene optical sample corresponds to at least a portion of a respective CSE optical sample.

17. The method of claim 16 further comprising:
    providing, by the FOB, the compressed optical samples to a sensor comprising a plurality of optical sensing elements (OSEs); and
    integrating, by each OSE, one or more received sensor optical samples, each sensor optical sample corresponding to at least a portion of a respective compressed optical sample.

18. The method of claim 17 further comprising:
    converting, by the sensor, the integrated received optical samples to electrical samples; and
    recovering, by a post processor, an image of the scene, based at least in part, on the electrical samples.

19. The method of claim 18 wherein a resolution of the recovered image of the scene is greater than a number of compressed optical samples.

20. The method of claim 16 further comprising:
    illuminating, by an illumination fiber, the scene.

21. The method of claim 20 wherein the illumination fiber is configured to provide at least one of infrared optical energy, ultraviolet optical energy and visible light to the scene.

22. The method of claim 16 wherein the CSO comprises at least one of a lens, a mirror, a microlens array, a micromirror array and a diffractive optical element.

* * * * *